(12) United States Patent
Cesana et al.

(10) Patent No.: US 9,862,664 B2
(45) Date of Patent: Jan. 9, 2018

(54) PROCESS FOR THE PRODUCTION OF ALKENOLS AND USE THEREOF FOR THE PRODUCTION OF 1,3-BUTADIENE

(71) Applicant: Versalis S.P.A., San Donato Milanese (IT)

(72) Inventors: Alberto Cesana, Galliate (IT); Stefano Ramello, Novara (IT); Guido Spano', Galliate (IT)

(73) Assignee: Versalis S.p.A., San Donato Milanese (IT)

( * ) Notice: Subject to any disclaimer, the term of this patent is extended or adjusted under 35 U.S.C. 154(b) by 0 days.

(21) Appl. No.: 15/303,640

(22) PCT Filed: May 15, 2015

(86) PCT No.: PCT/IB2015/053592
§ 371 (c)(1),
(2) Date: Oct. 12, 2016

(87) PCT Pub. No.: WO2015/173780
PCT Pub. Date: Nov. 19, 2015

(65) Prior Publication Data
US 2017/0057893 A1 Mar. 2, 2017

(30) Foreign Application Priority Data
May 16, 2014 (IT) .............................. MI2014A0897

(51) Int. Cl.
| | |
|---|---|
| *C07C 29/00* | (2006.01) |
| *C07C 1/00* | (2006.01) |
| *B01J 21/00* | (2006.01) |
| *C07C 29/60* | (2006.01) |
| *B01J 23/10* | (2006.01) |
| *C07C 1/24* | (2006.01) |
| *B01J 37/03* | (2006.01) |
| *B01J 35/00* | (2006.01) |
| *B01J 35/10* | (2006.01) |
| *B01J 37/00* | (2006.01) |
| *B01J 21/12* | (2006.01) |

(52) U.S. Cl.
CPC .............. *C07C 29/60* (2013.01); *B01J 21/12* (2013.01); *B01J 23/10* (2013.01); *B01J 35/002* (2013.01); *B01J 35/1009* (2013.01); *B01J 35/1014* (2013.01); *B01J 37/0036* (2013.01); *B01J 37/031* (2013.01); *C07C 1/24* (2013.01); *C07C 2521/12* (2013.01)

(58) Field of Classification Search
CPC .. C07C 29/60; C07C 1/24; B01J 21/12; B01J 23/10; B01J 35/00
USPC ....................................................... 568/840
See application file for complete search history.

(56) References Cited

U.S. PATENT DOCUMENTS

| | | | |
|---|---|---|---|
| 4,400,562 A | 8/1983 | Wagaman et al. | |
| 5,406,007 A | 4/1995 | Falling | |
| 6,228,799 B1 | 5/2001 | Aubert et al. | |
| 6,278,031 B1 | 8/2001 | Brocker et al. | |
| 7,259,280 B1 * | 8/2007 | Kahn ...................... | C07C 29/60 568/903 |
| 2010/0330635 A1 | 12/2010 | Burgard et al. | |
| 2012/0329113 A1 | 12/2012 | Burgard et al. | |
| 2013/0109064 A1 | 5/2013 | Osterhout et al. | |

FOREIGN PATENT DOCUMENTS

| | | |
|---|---|---|
| CN | 101759529 A | 6/2010 |
| DE | 1150671 B | 6/1963 |
| DE | 1908620 A1 | 9/1970 |
| JP | 63/222135 A | 9/1988 |
| SU | 396312 A1 | 8/1973 |
| WO | 2013/130481 A1 | 9/2013 |

OTHER PUBLICATIONS

He Y, et al. "Selective Catalytic Dehydration of 1,4-Butanediol to 3-Buten-1-ol over CeO2 with Different Morphology", Chinese Journal of Catalysis/Dalian Institute of Chemical Physics, Elsevier, Amsterdam, NL, vol. 31, No. 6, Jan. 1, 2010, pp. 619-622.

Djuricic B, et al. "Nanostructured cerium oxide: preparation and properties of weakly-agglomerated powders", Journal of the European Ceramic Society, Elsevier Science Publishers, Barkins, Essex, GB, vol. 19, No. 11, Sep. 1, 1999, pp. 1925-1934.

Hailing Duan, et al. "Dehydration of 2, 3-butanediol into 3-buten-2-ol catalyzed by ZrO2", Catalysis Communications, vol. 48, Mar. 1, 2014, pp. 1-4.

Sato S., et al. "Selective Dehydration of dials to allylic alchohols catalyzed by ceria", Catalysis Communications, Elsevier Science, Amsterdam, NL, vol. 4, No. 2, Jan. 1, 2003, pp. 77-81.

Diez V. K., et al. "Gas-phase conversion of 1, 3-butanediol on single acid-base of Cu-promoted ox", Catalysis Today, vol. 213, Apr. 18, 2013, pp. 18-24.

Ferretti C. A., et al. "Monoglyceride synthesis by glcerolysis of methyl oleate on solid acid-base catalysts", Chemical Engineering Journal, Elsevier Sequoia, Laussane, CH, vol. 161, No. 2, Jul. 15, 2010, pp. 346-354.

(Continued)

*Primary Examiner* — Sikarl Witherspoon
(74) *Attorney, Agent, or Firm* — Abel Law Group, LLP

(57) ABSTRACT

Process for the production of alkenols comprising the dehydration of at least one diol in the presence of at least one catalyst based on cerium oxide, wherein said catalyst based on cerium oxide is obtained by precipitation, in the presence of at least one base, of at least one compound containing cerium. Preferably, said diol may be a butanediol, more preferably 1,3-butanediol, still more preferably bio-1,3-butanediol derived from biosynthetic processes. Said alkenols may advantageously be used for the production of 1,3-butadiene, in particular of bio-1,3-butadiene.

23 Claims, No Drawings

(56) References Cited

OTHER PUBLICATIONS

Gräfje H. et al. in "Butanediols, Butenediol, and Butynediol", "Ullmann's Encyclopedia of Industrial Chemistry" (2000).

Winfield M. E. in "The catalytic Dehydration of 2,3-butanediol to Butadiene. II. Adsorption Equilibria", "Australian Journal of Scientific Research" (1950), vol. 3(2), pp. 290-305.

Sato S. et al., in "Applied Catalysis A: General" (2007), vol. 328, pp. 109-116.

Gotoh H. et al., in "Applied Catalysis A: General" (2010), vol. 377, pp. 92-98.

Igarashi A. et al., in "Applied Catalysis A: General" (2006), vol. 300, pp. 50-57.

Igarashi A. et al., "Applied Catalysis A: General" (2006), vol. 314, pp. 134.

A. R. Graham in "American Mineralogist" (1950), vol. 40, pp. 560-564.

Ricken M. et al., in "Specific heat and phase diagram of nonstoichiometric ceria ($CeO_{2-x}$)", "Journal of Solid State Chemistry" (1984), vol. 54, Issue 1, pp. 89-99.

Rohart E. et al., in "Topics in Catalysis" (2004), vol. 30-31, Issue 1-4, pp. 417-423.

Sato S. et al. In "Journal of Molecular Catalysis A: Chemical" (2006), vol. 256, pp. 106-112.

International Search Report for PCT/IB2015/05392 dated Aug. 12, 2015, 14 pgs.

* cited by examiner

PROCESS FOR THE PRODUCTION OF ALKENOLS AND USE THEREOF FOR THE PRODUCTION OF 1,3-BUTADIENE

The present invention relates to a process for the production of alkenols.

More particularly, the present invention relates to a process for the production of alkenols comprising the dehydration of at least one diol in the presence of at least one catalyst based on cerium oxide, wherein said catalyst based on cerium oxide is obtained by precipitation, in the presence of at least one base, of at least one compound containing cerium.

Preferably, said diol may be a butanediol, more preferably 1,3-butanediol, still more preferably bio-1,3-butanediol derived from biosynthetic processes.

Said alkenols may advantageously be used for the production of 1,3-butadiene, in particular of bio-1,3-butadiene.

The present invention also relates to a process for the production of 1,3-butadiene, in particular of bio-1,3-butadiene, comprising bringing at least one of the alkenols obtained with the above-stated process into contact with at least one catalyst, preferably an acid catalyst, under suitable conditions for the dehydration of said at least one alkenol.

In particular, the alkenols obtained by the above-stated process, i.e. 3-buten-2-ol (methyl vinyl carbinol—CAS Number 598-32-3), 3-buten-1-ol (allyl carbinol—CAS Number 627-27-0) or 2-buten-1-ol (crotyl alcohol), more particularly 2-buten-1-ol (crotyl alcohol) and 3-buten-2-ol (methyl vinyl carbinol—CAS Number 598-32-3), may advantageously be used for the production of 1,3-butadiene, in particular of bio-1,3-butadiene, or in the production of intermediates which may in they turn be used in fine chemistry, agricultural chemistry, pharmaceutical chemistry or in petrochemistry.

For the purpose of the present description and of the following claims, the term 2-buten-1-01 (crotyl alcohol) is taken to mean: either a mixture of the cis and trans isomers, or the cis isomer as such (CAS Number 4088-60-2), or the trans isomer as such (CAS Number 504-61-0).

It is known that, at present, the industrial production of 1,3-butanediol, 1,3-butadiene and alkenols is based on conventional petrochemical processes.

As a matter of fact, diols having four carbon atoms in general, and 1,3-butanediol (generally also denoted as 1,3-BDO) in particular, are generally obtained by means of complex petrochemical processes as described, for example by Gräfje H. et al. in "Butanediols, Butenediol, and Butynediol", *Ullmann's Encyclopedia of Industrial Chemistry* (2000). In particular, the 1,3-butanediol is produced via acetaldehyde, hydroxybutyraldehyde and subsequent reduction, and is generally used as a component of resins or as a solvent.

American U.S. Pat. No. 5,406,007 describes a process for the preparation of an allylic alcohol, a homoallylic alcohol, or a mixture thereof, comprising hydrogenating an epoxyalkene, wherein the epoxy group and the ethylenic unsaturation are conjugated, in the presence of a sulfur-modified or nickel sulphide catalyst, operating at conditions of temperature and of pressure typical of hydrogenation. Preferably, said process is useful for the preparation of a mixture of 2-buten-1-ol (crotyl alcohol) and 3-buten-1-ol. American U.S. Pat. No. 6,278,031 describes a process for the preparation of 2-buten-1-ol compounds having the formula (I):

$$H_2R^1\text{---}R^2C=CR^3\text{---}CR^4R^5\text{---}OR^6 \qquad (I)$$

wherein the $R^1$, $R^2$, $R^3$, $R^4$, $R^5$ and $R^6$ radicals, each independently, are hydrogen or an aliphatic radical optionally substituted with an OH or with a group OR wherein R is an aliphatic group, a halogen or a carboxyl group, furthermore $R^2$ represents a radical —CHO, or $R^2$ and $R^5$ together with the carbon atoms located in between form an alicyclic ring, and $R^6$ additionally represents a cycloaliphatic, araliphatic or aromatic radical or a radical —C(=O)—$R^7$ wherein $R^7$ is an aliphatic, cycloaliphatic, araliphatic or aromatic radical, said process comprising isomerising 3-buten-1-ol compounds having the formula (II):

$$HR^1C=CR^2\text{---}CHR^3\text{---}CR^4R^5\text{---}OR^6 \qquad (II)$$

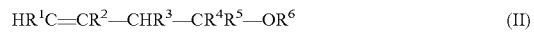

wherein the $R^1$, $R^2$, $R^3$, $R^4$, $R^5$ and $R^6$ radicals have the same meanings described above, in the presence of hydrogen and of a catalyst, wherein the process is carried out continuously on a fixed-bed catalyst, wherein the catalyst comprises palladium and selenium or tellurium or a mixture of selenium and tellurium on a silicon dioxide support, and has a BET surface area ranging from 80 m²/g to 380 m²/g and a pore volume ranging from 0.6 cm³/g to 0.95 cm³/g in a pore diameter ranging from 3 nm to 300 µm, with from 80% to 95% of the pore volume being in a pore diameter ranging from 10 nm to 100 nm.

Alternatively, 2-buten-1-ol (crotyl alcohol) may be prepared by reduction of crotonaldehyde as described, for example, in "Merck Index" (1976), 9th Edition. Furthermore, 2-buten-1-ol (crotyl alcohol) may be prepared by means of biosynthetic processes as described, for example, in international patent application WO 2013/130481 (as an intermediate in the synthesis of 1,3-butadiene), or in American patent application US 2013/109064.

American U.S. Pat. No. 4,400,562 describes a method for synthesizing an alkenol from 1,3-butanediol in the liquid phase comprising: admixing a trivalent metal sulfate selected from aluminium sulfate, chromium sulfate, iron sulphate, and mixtures thereof, as catalyst, with 1,3-butanediol in an effective amount to obtain a mixture of said catalyst suspended in 1,3-butanediol; heating said mixture to a temperature of about 70° C. below to about 100° C. above the boiling point of 1,3-butanediol, to achieve a partial dehydration of the 1,3-butanediol to 3-buten-1-ol which evaporates from the reaction mixture; and condensing said vapour to isolate 3-buten-1-ol.

Alternatively, 3-buten-1-ol may be prepared from propylene and formaldehyde, in the presence of a catalyst, operating at elevated temperatures, as described, for example, in American patent application US 2013/109064.

3-Buten-2-ol (methyl vinyl carbinol) and butadiene may be obtained by dehydration of 2,3-butanediol in the presence of thorium oxide as described, for example, by Winfield M. E. in "The catalytic Dehydration of 2,3-butanediol to Butadiene. II. Adsorption Equilibria", *Australian Journal of Scientific Research* (1950), Vol. 3(2), pp. 290-305.

Alternatively, 3-buten-2-ol (methyl vinyl carbinol), alone or in a mixture with other butenols, may be obtained for example: by thermal decomposition of polyols or the derivatives thereof (e.g., 1,3-butylene glycol diacetate) as described, for example, in german patent DE 1,150,671; or by reduction of acetylenes or of unsaturated carbonyl compounds as described, for example, in russian patent SU 396312 or in japanese patent application JP 63/222135.

2-Buten-1-ol (crotyl alcohol) may be used, for example, as a precursor of halides, crotyl esters or crotyl ethers which, in their turn, may be used, for example, as intermediates in the production of monomers, in fine chemistry (for example, for the production of sorbic acid, trimethylhydroquinone, crotonic acid, 3-methoxybutanol), in agricultural chemistry, or in pharmaceutical chemistry.

3-Buten-1-ol (allyl carbinol) may be used, for example, as a raw material in pharmaceutical chemistry, in agricultural chemistry, in perfumes, in resins. For example, aryl-substituted aldehydes which may be used in pharmaceutical chemistry, for example as folic acid antagonists, may be obtained from the coupling reaction of 3-buten-1-ol (allyl carbinol) with aryl halides, catalysed by palladium.

3-Buten-2-ol (methyl vinyl carbinol) may be used as a solvent, in fine chemistry, as a component in the modification of polymers such as, for example, polyolefins (as described, for example, in german patent DE 1,908,620).

The above-stated alkenols may also be used for the production of 1,3-butadiene. 1,3-Butadiene is a basic product of petrochemistry. Around ten million tonnes of 1,3-butadiene are produced annually and preferentially used in the production of various products such as, for example, synthetic rubbers, resins, acrylonitrile-butadiene-styrene (ABS) terpolymers, hexamethylenediamine, butanediols, in particular, 1,4-butanediol. More than 95% of the 1,3-butadiene produced annually is a by-product derived from steam cracking processes for the production of ethylene and other olefins and is separated by extractive distillation. Production processes of 1,3-butadiene "on-purpose" which may be mentioned are, for example, the dehydrogenation of butane and/or butenes.

The possibility of developing alternative production processes of alkenols and 1,3-butadiene which are efficient, have high productivity, low production costs and reduced environmental impact, still remains of great interest. In particular, new processes capable of using materials derived from biosynthetic processes, for example bio-1,3-butanediol, to yield, by catalytic dehydration, bio-alkenols which may in their turn be used for the production of bio-1,3-butadiene are certainly of interest.

Carbon sources which may be used in said biosynthetic processes are preferably renewable sources, biomass, syngas or other gaseous carbon sources.

Syngas may be obtained by processes known in the art by gasifying materials containing carbon (such as, for example, coal, biomasses, waste, natural gas, and the like).

Said biosynthetic processes are generally performed by way of microorganisms which are capable of using carbon sources such as, for example, carbohydrates. Carbohydrate sources which may be mentioned are, for example, sugars (glucose, xylose, arabinose, fructose, and the like), biomasses (cellulosic, hemicellulosic, lignin, and the like), preferably containing carbohydrates, other renewable sources.

Catalysts based on cerium oxide and the use thereof for the dehydration of diols and butanediols to alkenols, are known in the art.

For example, Sato S. et al., in "*Catalysis Communications*" (2003), Vol. 4, pp. 77-81, describe the selective dehydration of diols to allyl alcohols [i.e. 2-buten-1-ol (crotyl alcohol) and 3-buten-2-ol (allyl carbinol)] catalysed by cerium oxides obtained commercially or by dehydration of citrates. In particular, they describe the selective dehydration catalysed by cerium oxide ($CeO_2$) of 1,3-butanediol to allyl alcohols (i.e. alkenols) operating at temperatures ranging from 300° C. to 375° C. In particular, in the dehydration of 1,3-butanediol catalysed by cerium oxide ($CeO_2$), operating at 325° C., 2-buten-1-ol (crotyl alcohol) and 3-buten-2-ol (methyl vinyl carbinol) are produced with high selectivity values (the total of alkenols produced is indeed greater than 99.7% mol as shown in Table 1), but with low conversion values (values ranging from 43.9% to 61% as shown in Table 1). Furthermore, cerium oxide ($CeO_2$) performs well and does not undergo any decay over the first 5 hours when using temperatures of less than 375° C., while a decay is observed over the first 5 hours when using a temperature equal to 400° C. (as shown in Figure 2). Only operating at a temperature equal to 375° C. a conversion of greater than 90%, still not complete, and a selectivity for allyl alcohols close to about 90% is reported (as shown in Figure 1 and in Figure 2). Said results are obtained in the presence of large quantities of diluent, i.e. nitrogen ($N_2$): indeed a 1,3-butanediol:nitrogen ($N_2$) ratio equal to 0.3 is used.

Sato S. et al., in "*Applied Catalysis A: General*" (2007), Vol. 328, pp. 109-116, describe the vapour phase reaction of 1,3-butanediol catalysed by commercial rare earth oxides derived from the decomposition of the corresponding chlorides at temperatures >2000° C., for about 2 hours, in the vapour phase. During said reaction of 1,3-butanediol, either dehydration to unsaturated alcohols or the formation of by-products occur simultaneously at 325° C. It is evident from the data shown in Table 2 that only commercial cerium oxide ($CeO_2$) used at a temperature equal to 325° C. and under the other operating conditions described therein is capable of providing good values for selectivity to alkenols [values of equal to 58% for 3-buten-2-ol (allyl carbinol) and 39.1% for 2-buten-1-ol (crotyl alcohol)] although with low conversion values (value equal to 27.9%), while the remaining catalysts exhibit low conversion and/or selectivity values.

Gotoh H. et al., in "*Applied Catalysis A: General*" (2010), Vol. 377, pp. 92-98, describe the vapour phase dehydration of 1,3-butanediol catalysed by commercial rare earth oxides derived from the decomposition of the corresponding chlorides at elevated temperatures and calcined at a different temperature (temperature ranging from 500° C. to 1000° C.) and thus having different crystalline structures. In particular, the use of cerium oxide ($CeO_2$) with a cubic crystalline structure (fluorite) provides the highest rate of formation of unsaturated alcohols at all calcination temperatures (as shown in Figure 3).

Higarashi A. et al., in "*Applied Catalysis A: General*" (2006), Vol. 300, pp. 50-57, and in "*Applied Catalysis A: General*" (2006), Vol. 314, pp. 134, describe the dehydration of butanediols to unsaturated alcohols catalysed by commercial cerium oxides ($CeO_2$) in powder form having different surface areas. In the dehydration of 1,3-butanediol, catalytic performances prove to be strongly influenced by surface area (as shown in Figure 4). Indeed, selectivity for unsaturated alcohols such as 3-buten-2-ol (methyl vinyl carbinol) and 2-buten-1-ol (crotyl alcohol, sum of cis and trans forms), decreases as surface area increases. Conversely, 1,3-butanediol conversion increases as surface area increases. It is evident from the data shown that, under the operating conditions used, it is not possible (as shown in Table 2, Table 3, Figure 5 and Figure 6) to achieve simultaneously elevated selectivities and elevated conversions, even when parameters such as temperature and contact time are varied.

However, the above-mentioned processes may have some drawbacks. Indeed, said processes are generally carried out in the presence of large quantities of diluent such as, for example, nitrogen ($N_2$), for example using a molar ratio of 1,3-butanediol:nitrogen ($N_2$) equal to 0.3, and are therefore not readily applicable industrially, not least due to the difficulty of recovering the alkenols of interest in large flows of gas such as nitrogen ($N_2$). Furthermore, the catalysts used in the above-stated processes are commercial materials in powder form, or are produced by processes which are not readily applicable for the purposes of industrial catalysis. For example, as mentioned above, said catalysts are derived from processes involving decomposition of the corresponding chlorides at elevated temperatures, or from processes involving the thermal decomposition of citrates and these are complex and/or costly processes. Consequently, any industrial use thereof would increase process costs. Furthermore, some of said catalysts, appropriately pre-treated, lead to an increase in selectivity for unsaturated alcohols but a reduction in conversion: consequently, for the purpose of industrial application, it would be necessary to use a large quantity of catalyst with consequent negative repercussions on capital and process costs.

As stated above, since, at present, the production of 1,3-butanediol, 1,3-butadiene and alkenols is based on conventional petrochemical approaches, new processes capable of producing said compounds using materials derived from biosynthetic processes are certainly of interest. In particular, there is certainly interest in finding a process wherein a diol, more preferably 1,3-butanediol, still more preferably bio-1,3-butanediol derived from biosynthetic processes, is subjected to dehydration to obtain bio-alkenols which may in their turn be used for the production of 1,3-butadiene, in particular bio-1,3-butadiene. The Applicant therefore set itself the problem of finding a process for the production of alkenols, in particular a process capable of using materials derived from biosynthetic processes, capable of overcoming the above-described drawbacks and capable of providing large quantities of alkenols, in particular bio-alkenols, which may subsequently be used, in particular, for the production of 1,3-butadiene, more in particular bio-1,3-butadiene.

The Applicant has now found that using a catalyst based on cerium oxide obtained by precipitation, in the presence of at least one base, of at least one compound containing cerium, in a process for the dehydration of at least one diol, preferably of at least one butanediol, more preferably 1,3-butanediol, still more preferably bio-1,3-butanediol derived from biosynthetic processes, enables the above-stated drawbacks to be overcome.

Numerous advantages are achieved by using the above-stated catalyst in the dehydration process. For example, said catalyst makes it possible to achieve elevated values for conversion, selectivity and productivity. Furthermore, said catalyst exhibits an extended service life, even when used in the presence of small quantities of diluent, i.e. at a diol: diluent ratio of greater than 0.3. Furthermore, said advantages are retained when using a wide temperature range which may extend to elevated values (e.g., values greater than or equal to 400° C.). The resultant alkenols may advantageously be used for the production of 1,3-butadiene, in particular of bio-1,3-butadiene.

The present invention accordingly provides a process for the production of alkenols comprising the dehydration of at least one diol, preferably of at least one butanediol, more preferably 1,3-butanediol, still more preferably bio-1,3-butanediol derived from biosynthetic processes, in the presence of at least one catalyst based on cerium oxide, wherein said catalyst based on cerium oxide is obtained by precipitation, in the presence of at least one base, of at least one compound containing cerium.

For the purpose of the present description and of the following claims, unless stated otherwise, definitions of numerical ranges always include the extremes.

For the purpose of the present description and of the following claims, the term "comprising" also encompasses the terms "which essentially consists of" or "which consists of".

According to a preferred embodiment of the present invention, said process for the production of alkenols may be carried out in the presence of at least one diluent. According to a preferred embodiment of the present invention, said catalyst based on cerium oxide may be obtained by a process comprising:
preparing a solution including at least one compound containing cerium;
adding to said solution at least one base in a time ranging from 1 minute to 16 hours, preferably ranging from 5 minutes to 2 hours, to obtain a reaction mixture;
allowing said reaction mixture to react at a temperature ranging from 15° C. to 100° C., preferably ranging from 20° C. to 65° C., for a time ranging from 1 minute to 120 hours, preferably ranging from 5 minutes to 110 hours, still more preferably ranging from 2 hours to 100 hours, to obtain a precipitate;
recovering the precipitate and subjecting it to drying and, optionally, to calcination.

According to a further embodiment of the present invention, said catalyst based on cerium oxide may be obtained by a process comprising:
preparing a solution including at least one base;
adding to said solution at least one compound containing cerium in a time ranging from 1 minute to 16 hours, preferably ranging from 5 minutes to 2 hours, to obtain a reaction mixture;
allowing said reaction mixture to react at a temperature ranging from 15° C. to 100° C., preferably ranging from 25° C. to 65° C., for a time ranging from 1 minute to 120 hours, preferably ranging from 5 minutes to 110 hours, still more preferably between ranging from 2 hours to 100 hours, to obtain a precipitate;
recovering the precipitate and subjecting it to drying and, optionally, to calcination.

It should be noted that, for the purpose of the present invention, said base and/or said compound containing cerium, may be added in one or more stages. For example, said base may be added in part to the solution including at least one compound containing cerium to obtain a reaction mixture to which is added, during the reaction, the remainder of said base. Or, said compound containing cerium may be added in part to the solution including at least one base to obtain a reaction mixture to which is added, during the reaction, the remainder of said compound containing cerium. Or, said compound containing cerium may be added to the solution including part of said base to obtain a reaction mixture to which is added, during the reaction, the remainder of said base. Or, said base may be added to the solution including part of said compound containing cerium to obtain a reaction mixture to which is added, during the reaction, the remainder of said compound containing cerium. The base and/or the compound containing cerium may be added using methods known in the art, as well as by making reference to standard laboratory practice (by way of example, but without limiting the scope of the present invention, by weighing out, volumetric metering, etc.). There may, however, be more than two stages of addition of the base and/or the compound containing cerium, but this is not in any way a critical feature and, hence, does not limit the present invention. According to one embodiment of the present invention, said solution including at least one compound containing cerium or said solution including at least one base, is an aqueous solution comprising from 5% by weight to 70% by weight, preferably from 10% by weight to 60% by weight, still more preferably from 15% by weight to 50% by weight, relative to the total weight of said aqueous solution, of at least one compound containing cerium or of at least one base.

According to a further embodiment of the present invention, said solution including at least one compound containing cerium or said solution including at least one base is a water-alcohol solution comprising from 5% by weight to 95% by weight, preferably from 15% by weight to 60% by weight, still more preferably from 10% by weight to 30% by weight, relative to the total weight of said water-alcohol solution, of at least one alcohol selected from ethanol, 2-methoxyethanol, n-propanol, iso-propanol, n-butanol, iso-butanol, tert-butanol, or mixtures thereof.

According to a preferred embodiment of the present invention, said compound containing cerium may be selected from: soluble cerium salts such as, for example, cerium salts of organic or inorganic acids such as, for example, cerium nitrate, cerium sulfate, cerium acetate, cerium chloride, cerium ammonium nitrate, or mixtures thereof; or cerium alkoxides such as, for example, cerium (IV) tert-butoxide, cerium(IV) 2-methoxyethoxide, cerium (IV) iso-propoxide, or mixtures thereof. Cerium salts of organic or inorganic acids are preferred, cerium nitrate is particularly preferred. For this purpose, it is preferable to use a cerium salt having a purity of at least 90%, preferably of at least 97%, more preferably of at least 98%.

According to a further embodiment of the present invention, in the case in which said solution containing at least one compound containing cerium mainly comprises cerium(III), at least one oxidising agent such as, for example, an aqueous solution of hydrogen peroxide, may optionally be added to said solution.

According to a further embodiment of the present invention, in the case in which said solution containing at least one compound containing cerium mainly comprises cerium(III), the recovered precipitate, before being subjected to drying and, optionally, calcination, may optionally be treated with at least one oxidising agent such as, for example, an aqueous solution of hydrogen peroxide.

According to a preferred embodiment of the present invention, said base may be selected, for example, from: hydroxides of alkali metals or alkaline earth metals such as, for example, sodium hydroxide, potassium hydroxide; secondary or tertiary amines such as, for example, diethylamine, trimethylamine; quaternary ammonium salts such as, for example, tetrapropylammonium hydroxide; ammonium hydroxide (NH$_4$OH), urea. More preferably, said base is used in the form of a solution, still more preferably it is selected from aqueous solutions of: ammonium hydroxide (NH$_4$OH), triethylamine, tetrapropylammonium hydroxide. Aqueous solutions of ammonium hydroxide (NH$_4$OH) are particularly preferred.

The pH value of said reaction mixture (i.e. of the reaction mixture comprising at least one compound containing cerium and at least one base) is preferably ranging from 7.5 to 14.0, more preferably ranging from 8.0 to 12.0, still more preferably ranging from 8.5 to 11.0.

The resultant precipitate may be recovered through processes known in the art such as, for example, filtration, decantation.

The resultant precipitate may be dried at temperature ranging from 100° C. to 200° C., preferably ranging from 105° C. to 150° C., for a time ranging from 2 hours to 72 hours, preferably ranging from 3 hours to 18 hours and, optionally, subjected to calcination. Said calcination may be carried out at temperature ranging from 150° C. to 1500° C., preferably ranging from 200° C. to 1400° C., still more preferably ranging from 300° C. to 1200° C., for a time ranging from 1 hour to 24 hours, preferably ranging from 2 hours to 10 hours, still more preferably ranging from 4 hours to 8 hours. Generally, said calcination may be carried out in air, or in the presence of an inert gas [for example, nitrogen (N$_2$)] or under a controlled (oxidising or reducing) atmosphere.

According to a preferred embodiment of the present invention, said catalyst based on cerium oxide may have a specific surface area ranging from 0.5 m$^2$/g to 250 m$^2$/g, preferably ranging from 1 m$^2$/g to 100 m$^2$/g, still more preferably ranging from 2 m$^2$/g to 60 m$^2$/g.

For the purpose of the present description and of the following claims, the term "specific surface area" denotes the BET specific surface area determined by static absorption of nitrogen (N$_2$) at a temperature of the liquid nitrogen equal to −196.15° C. (77 K), using a Micromeritics ASAP 2010 instrument, in accordance with standard ASTM D3663-03 (2008).

Said catalyst based on cerium oxide has also been characterised by means of X-ray diffractometry (XRD) using a Philips X'Pert θ/2θ automatic powder diffractometer with Bragg-Brentano geometry using Cu-Kα X-radiation with λ=1.5416 Å and a power of 1.6 kW. The angular range used extends from 5° to 90° (2θ) with 0.02° (2θ) steps and an acquisition time equal to 2 seconds per-step. Furthermore, the presence of cerium oxide was detected using the information present in the PDF-4 ("Powder Diffraction File") database published by ICDD® ("The International Centre for Diffraction Date"). Cerium oxide, otherwise known as cerianite [as described, for example, by A. R. Graham in "*American Mineralogist*" (1950), Vol. 40, pp. 560-564], is a crystalline oxide of a cubic, face-centred structure of the fluorite type and may be identified by means of diffractograms present in reference cards present in the above-mentioned PDF-4 database, such as, for example, the cards designated 04-001-2097, 04-018-4610, 01-078-3280, 04-008-6551. Said reference cards show cerium oxides having an identical structure and a variable stoichiometry of the type CeO$_{2-x}$, wherein x is ranging from 0 to 0.4. It is indeed known that cerium(IV) oxide may have a defective, oxygen-deficient stoichiometry as described, for example, by Ricken M. et al., in "Specific heat and phase diagram of nonstoichiometric ceria (CeO$_{2-x}$)", "*Journal of Solid State Chemistry*" (1984), Vol. 54, Issue 1, pp. 89-99.

Said catalyst based on cerium oxide may be used in various forms. For example, said catalyst based on cerium oxide may be used as such, or may be formed using any forming process known in the art such as, for example, extrusion, spherulisation, tabletting, granulation, and the like. The above-stated drying and calcination may be performed before or after one of said forming processes.

According to a preferred embodiment of the present invention, said catalyst based on cerium oxide may be used in the form of an extrudate, optionally containing conventional binders such as, for example, aluminium oxide, silicon oxide, zirconium oxide.

In the case in which said conventional binders are present, extrusion generally also provides the use of a peptising agent such as, for example, aqueous solutions of acetic acid, of nitric acid, or of ammonium hydroxide, which may be mixed with the catalyst and the binder prior to extrusion until a homogeneous mixture is obtained. On completion of said extrusion, the resultant pellets are generally subjected to calcination carried out as described above.

As described in the art, for example, by Rohart E. et al., in "Topics in Catalysis" (2004), Vol. 30-31, Issue 1-4, pp. 417-423, and in American patent U.S. Pat. No. 6,228,799, cerium oxide may be used in a solid solution with zirconium oxide in order to maintain elevated reactivity even under severe conditions, such as for example those required by TWC ("Three Way Catalyst") applications in exhaust gas treatment.

Consequently, the catalyst based on cerium oxide used in the process of the present invention may also be stabilised with zirconium oxide. In this case, the catalyst (mixed cerium and zirconium oxide) will have the general formula:

$$(1-x)CeO_2\text{-}xZrO_2$$

wherein, preferably $x<0.5$, more preferably $x<0.2$.

According to a particularly preferred embodiment of the present invention, said diol is bio-1,3-butanediol derived from the fermentation of sugars, preferably from the fermentation of sugars derived from biomass.

For the purpose of the present description and of the following claims, the term "biomass" denotes any organic material of vegetable origin including: products derived from agriculture such as, for example, guayule, thistle, maize, soy, cotton, flax, rape, sugar cane, palm, including discards, residues and waste derived from said products or the processing thereof; products derived from crops specifically grown for energy use such as, for example, miscanthus, panic grass, giant cane, including discards, residues and waste derived from said products or the processing thereof; products derived from forestry or silviculture, including discards, residues and waste derived from said products or the processing thereof; discards from agricultural products intended for human food or animal feedstuffs; residues from the paper industry; waste originating from separate collection of solid urban waste, such as, for example, urban waste of vegetable origin, paper.

In accordance with one particularly preferred embodiment of the present invention, said diol is bio-1,3-butanediol derived from the fermentation of sugars obtained from guayule or thistle, including discards, residues or waste derived from said guayule and/or thistle or the processing thereof.

In accordance with one particularly preferred embodiment of the present invention, said diol is bio-1,3-butanediol derived from the fermentation of sugars obtained from guayule, including discards, residues or waste derived from said guayule or the processing thereof.

When lignocellulosic biomass of vegetable origin is used to produce sugars, said biomass is subjected to physical treatments (for example, extrusion, steam explosion, and the like), and/or to chemical hydrolysis and/or to enzymatic hydrolysis, giving rise to mixtures of carbohydrates, aromatic compounds and other products derived from the cellulose, hemicellulose and lignin present in the biomass. In particular, the resultant carbohydrates are mixtures of sugars with 5 and 6 carbon atoms which include, for example, sucrose, glucose, xylose, arabinose, galactose, mannose and fructose, which will be used in fermentation. Processes relating to the production of biomass sugars are described in the art such as, for example, in Italian patent application MI2013A002069, in the name of the present Applicant. Said fermentation is generally performed by microorganisms, in particular by genetically modified microorganisms, capable of producing the alcohols of interest. Further details relating to processes for the synthesis of 1,3-butanediol, in particular bio-1,3-butanediol, starting from renewable sources may be found, for example, in american patent applications US 2010/330635, US 2012/0329113 and US 2013/0109064.

As stated above, said process for the production of alkenols may be carried out in the presence of at least one diluent.

According to a preferred embodiment of the present invention, said diluent may be selected, for example, from: inert gases such as, for example, nitrogen ($N_2$), argon (Ar), preferably nitrogen ($N_2$); or from compounds having a boiling point greater than or equal to 50° C. and a melting temperature of less than or equal to 40° C., which are preferably in the liquid state at room temperature (25° C.) and at ambient pressure (1 atm), such as, for example, water, tetrahydrofuran, cyclohexane, benzene. Nitrogen ($N_2$), water, are preferred, water is particularly preferred.

It should be noted that, in the case in which the diol is derived from biosynthetic processes, for example, from the fermentation of sugars, the aqueous solution originating from said biosynthetic processes or from said fermentation may be used, in fact using the water as diluent, without any need to subject said aqueous solution to costly processes for removing water or, any event, limiting such removal.

According to a preferred embodiment of the present invention, said process for the production of alkenols may be carried out, in the case in which the diluent is selected from inert gases, at a molar ratio between diol and diluent greater than 0.3, preferably ranging from 0.5 to 2.

According to a preferred embodiment of the present invention, said process for the production of alkenols may be carried out, in the case in which the diluent is selected from compounds having a boiling point greater than or equal to 50° C. and a melting temperature of less than or equal to 40° C., which are preferably in the liquid state at room temperature (25° C.) and at ambient pressure (1 atm), at a molar ratio between diol and diluent ranging from 0.1 to 100, preferably ranging from 0.4 to 10, more preferably ranging from 0.5 to 2.

According to a further particularly preferred embodiment of the present invention, said process for the production of alkenols may be carried out at a molar ratio between diol and diluent equal to 1.

According to a preferred embodiment of the present invention, said process for the production of alkenols may be carried out at a temperature ranging from 200° C. to 500° C., preferably ranging from 250° C. to 450° C., more preferably ranging from 300° C. to 430° C.

According to a preferred embodiment of the present invention, said process for the production of alkenols may be carried out at a pressure ranging from 0.05 bara to 50 bara, preferably ranging from 0.3 bara to 3.5 bara, more preferably ranging from 0.8 bara to 2.5 bara (bara=bar absolute).

According to a preferred embodiment of the present invention, said process for the production of alkenols may be carried out operating at a "Weight Hourly Space Velocity" (WHSV), i.e. at a ratio between the weight of the diol fed in one hour and the weight of catalyst based on cerium oxide, said ratio being measured in $h^{-1}$, ranging from 0.5 $h^{-1}$ to 20 $h^{-1}$, preferably ranging from 2 $h^{-1}$ to 15 $h^{-1}$, more preferably ranging from 5 $h^{-1}$ to 12 $h^{-1}$.

According to a preferred embodiment of the present invention, said catalyst based on cerium oxide may be pre-treated at the temperature at which said process for the production of alkenols is carried out, i.e. at a temperature ranging from 200° C. to 500° C., preferably ranging from 250° C. to 450° C., more preferably ranging from 300° C. to 430° C. For the purpose of the present invention, said process for the production of alkenols may be carried out in the gas phase or in a mixed liquid/gas phase, preferably in the gas phase, discontinuously (for example, in a stirred and heated autoclave), or continuously (for example, in one or more catalytic reactors in series), preferably continuously. Said reactors may be of the fixed-bed or fluidised-bed type, preferably of the fixed-bed type. In the case in which they are fixed-bed reactors, the catalyst based on cerium oxide may be subdivided between a plurality of beds. Said reactors may involve recirculation of a part of the effluents from the reaction or of the catalyst based on cerium oxide by a recirculating reactor being provided. In the case in which a liquid phase is present, the process for the production of alkenols may be carried out in a continuous, stirred reactor containing the catalyst based on cerium oxide in a dispersion.

As has been stated above, the alkenols obtained by the above-stated process, i.e. 3-buten-2-ol (methyl vinyl carbinol—CAS number 598-32-3), 3-buten-1-ol (allyl carbinol—CAS number 627-27-0) or 2-buten-1-ol (crotyl alcohol), more particularly 2-buten-1-ol (crotyl alcohol) and 3-buten-2-ol (methyl vinyl carbinol—CAS number 598-32-3), may advantageously be used for the production of 1,3-butadiene, in particular of bio-1,3-butadiene, or in the production of intermediates which may in their turn be used in fine chemistry, agricultural chemistry, pharmaceutical chemistry, or in petrochemistry.

Before being used for the production of 1,3-butadiene, the alkenols obtained by the above-stated process may be subjected to separation by means of processes known in the art, for example by means of distillation, complete or partial, of the reaction effluent (i.e. of the mixture containing said alkenols obtained by the above-stated process).

Alternatively, said alkenols (i.e. the mixtures containing said alkenols obtained from the above-stated process) may be used directly, i.e. without being subjected to separation, for the production of 1,3-butadiene.

The production of 1,3-butadiene from alkenols may be performed by processes known in the art. For example, butadiene may be produced from alkenols by dehydration of the alkenols in the presence of an acid catalyst such as, for example, $SiO_2$—$Al_2O_3$, as described, for example, by Sato S. et al. in "*Journal of Molecular Catalysis A: Chemical*" (2006), Vol. 256, pp. 106-112; or as described, in particular in the case of 2-buten-1-ol (crotyl alcohol), in the above-mentioned international patent application WO 2013/130481.

The present invention further provides a process for the production of 1,3-butadiene, in particular of bio-1,3-butadiene, comprising bringing at least one of the alkenols obtained with the above process, preferably 2-buten-1-ol (crotyl alcohol) and/or 3-buten-2-ol (methyl vinyl carbinol), into contact with at least one catalyst, preferably an acid catalyst, under suitable conditions for the dehydration of said at least one alkenol.

Said catalyst is preferably selected from solid acid catalysts such as, for example, silica-aluminas, silicas, aluminas, zeolites, or mixtures thereof.

For the purpose of the present invention and of the following claims, the term "zeolites" is taken to have its widest meaning, i.e. also comprising those materials conventionally known, for example, as "zeolite-like", "zeo-type", and the like.

Preferably, said process for the production of 1,3-butadiene may be carried out in the gas phase or in a mixed liquid/gas phase, more preferably in the gas phase, and still more preferably, continuously (for example, in one or more catalytic reactors in series). Said reactors may be of the fixed-bed or fluidised-bed type and are preferably of the fixed-bed type. In the case in which the reactors are of the fixed-bed type, the catalyst may be subdivided between a plurality of beds. Said reactors may involve recirculation of a part of the effluents from the reaction or of the catalyst by a recirculating reactor being provided.

Preferably, said process for the production of 1,3-butadiene, in particular of bio-1,3-butadiene, may be carried out at a temperature ranging from 150° C. to 500° C., preferably ranging from 250° C. to 450° C.

Some illustrative, non-limiting examples of the present invention are provided below to assist in understanding the present invention and the implementation thereof.

EXAMPLE 1

Preparation of a Catalyst Based on Cerium Oxide in the Presence of a Base

A solution of 87 g of cerium nitrate hexahydrate (99.9% Acros; product code 218695000; CAS Number 10294-41-4) in 420 g of water was prepared by vigorous stirring, at room temperature (25° C.), in a 1 liter beaker equipped with a magnetic stirrer bar. With vigorous stirring being maintained, 77 g of a 15% aqueous ammonium hydroxide ($NH_4OH$) solution, previously prepared by diluting the 30% commercial aqueous solution (Carlo Erba, 30% RPE-ACS ammonia solution; product code 419941, CAS Number 1336-21-6), were added to the resultant solution over a period of 25 minutes by means of a peristaltic pump, with pH being monitored by way of a Hamilton LIQ-GAS combined glass laboratory pH electrode connected to a EUTECH Instruments pH1500 pH meter. On completion of the addition of said solution, a suspension having a pH equal to 9.0 was obtained. Vigorous stirring of the mixture was continued for 64 hours. Subsequently, with vigorous stirring being maintained, a further 34 g of 15% aqueous ammonium hydroxide ($NH_4OH$) solution, previously prepared as described above, were added to the resultant suspension, having a pH equal to 4.0, over a period of 10 minutes by means of a peristaltic pump, a suspension having a pH equal to 9.0 being obtained. The suspension was vigorously stirred for a further 24 hours, at the end of which period the pH was remeasured and found to be equal to 8.9, and a precipitate was obtained. The resultant precipitate was filtered, washed with 500 ml of water, and subsequently dried in an oven at 120° C. for 2 hours. After drying, the resultant solid was calcined for 6 hours at 1000° C. The XRD spectrum of the solid obtained after calcination revealed the formation of a catalyst based on crystalline cerium oxide (identified by comparison with reference card 04-008-6551 present in the PDF-4 database which has already been mentioned above). The resultant catalyst based on cerium oxide had a BET specific surface area, determined as mentioned above, equal to 4 $m^2/g$.

EXAMPLE 2

Preparation of a Catalyst Based on Cerium Oxide in the Presence of a Base

A solution of 870 g of cerium nitrate hexahydrate (99% Aldrich; product code 238538; CAS Number 10294-41-4) in 4200 g of water was prepared by vigorous stirring, at room temperature (25° C.), in a glass beaker equipped with a magnetic stirrer bar. The resultant solution was transferred into a glass reactor equipped with an anchor stirrer and stirring was maintained for 15 minutes. With stirring being maintained, 790 g of an aqueous 15% ammonium hydroxide (NH$_4$OH) solution, previously prepared by diluting the 28%-30% commercial aqueous solution (Aldrich 28%-30% NH$_3$ Basis ACS reagent; product code 221228, CAS Number 1336-21-6), were added to the resultant solution over a period of 3 hours by means of a peristaltic pump, with pH being monitored by way of a Metrohm glass pH electrode (6.0248.030) connected to a Metrohm 691 pH meter. On completion of the addition of said solution, the pH of the suspension was equal to 9.0, stirring was continued under the same conditions for 64 hours, at the end of which period the pH was found to be equal to 4.3. Subsequently, with stirring being maintained, a further 90 g of a 15% aqueous ammonium hydroxide (NH$_4$OH) solution, previously prepared as described above, were added to the resultant suspension over a period of 25 minutes by means of a peristaltic pump, a suspension with a pH equal to 9.0 being obtained. The suspension was vigorously stirred for a further 24 hours, at the end of which period the pH was remeasured and found to be equal to 8.8, and a precipitate was obtained. The resultant precipitate was filtered, washed with about 10 liters of water, and subsequently dried in an oven at 120° C. for 2 hours. After drying, the resultant solid was calcined for 6 hours at 600° C.

The XRD spectrum of the solid obtained after calcination revealed the formation of a catalyst based on crystalline cerium oxide (identified by comparison with reference card 04-008-6551 present in the PDF-4 database which has already been mentioned above). The resultant catalyst based on cerium oxide had a BET specific surface area, determined as mentioned above, equal to 19 m$^2$/g.

EXAMPLE 3

Preparation of a Catalyst Based on Cerium Oxide in the Presence of a Base 200 g of an approximately 30% commercial aqueous ammonium hydroxide (NH$_4$OH) solution, (Aldrich 28%-30% NH$_3$ Basis ACS reagent; product code 221228; CAS Number 1336-21-6) were added in a 1 liter beaker equipped with a Teflon half-moon paddle stirrer and an electrode for measuring pH [Metrohm glass pH electrode (6.0248.030), connected to a Metrohm 780 pH meter] was introduced. A solution of 200 g of cerium nitrate hexahydrate (99% Aldrich; product code 238538; CAS Number 10294-41-4) in 200 g of water was prepared in another 500 ml beaker equipped with a magnetic stirrer bar: the cerium nitrate was then dissolved by vigorous stirring at room temperature (25° C.). The resultant solution was introduced into a dropping funnel and dispensed dropwise in 6 minutes into the above-mentioned ammonium hydroxide solution present in the 1 liter beaker with constant vigorous stirring. The pH of the resultant suspension was equal to 10.1. Vigorous stirring of the mixture was continued for 3 hours, after which 200 ml of water were added and the pH was measured and found to be equal to 9.6. Vigorous stirring of the mixture was continued for a further 1.5 hours, at the end of which period a further 200 ml of water were added and the pH was measured and found to be equal to 9.5. Said suspension was vigorously stirred for 64 hours, at the end of which period the pH was remeasured and found to be equal to 4.5. Subsequently, a further 23 g of approximately 30% ammonium hydroxide (NH$_4$OH) (Aldrich 28%-30% NH$_3$ Basis ACS reagent; product code 221228; CAS Number 1336-21-6) were added, a pH equal to 9.0 being obtained: stirring of the mixture was continued for 6 hours, a pH equal to 8.5 being obtained. Subsequently, 16 g of approximately 30% ammonium hydroxide (NH$_4$OH) (Aldrich 28%-30% NH$_3$ Basis ACS reagent; product code 221228; CAS Number 1336-21-6) were added, a pH equal to 9.0 being obtained. Vigorous stirring of the mixture was continued for 17 hours, at the end of which period the pH was equal to 7.9 and a precipitate was obtained. The resultant precipitate was filtered, washed with 2 liters of water, and subsequently dried in oven at 120° C. for 2 hours. After drying, the resultant solid was calcined for 5 hours at 600° C.

The XRD spectrum of the solid obtained after calcination revealed the formation of a catalyst based on crystalline cerium oxide (identified by comparison with reference card 04-008-6551 present in the PDF-4 database which has already been mentioned above). The resultant catalyst based on cerium oxide had a BET specific surface area, determined as mentioned above, equal to 49 m$^2$/g.

EXAMPLE 4

Preparation of Alkenols by Dehydration of 1,3-Butanediol

Catalytic activity tests were carried out in the experimental apparatus and using the operating methods described below.

The 1,3-butanediol dehydration reaction was performed in a fixed-bed tubular reactor of AISI 316L steel, with a length of 400 mm and an internal diameter of 9.65 mm. Within the reactor, along the axis thereof, there was a well with an external diameter of 3 mm which accommodated the thermocouple for controlling temperature. The reactor was placed in an electrically heated oven capable of reaching the temperature selected for the above-stated reaction. The catalysts used in the tests were ground and then sieved to obtain the 0.5 mm to 1 mm fraction.

The catalyst charge of 3 g was placed in the above-stated reactor between two layers of inert material (corundum), the catalyst bed was held in place by means of a sintered steel baffle placed on the bottom of the reactor which has a downward flow ("down-flow reactor").

Feed was performed from the top of the reactor, above the zone filled with inert material which acted as an evaporator and enabled the reactants to reach reaction temperature before coming into contact with the catalyst.

The liquid reactants were fed by a metering pump of the type used in high-performance liquid chromatography (HPLC). The gas were fed by "thermal mass flow meter" (TMF). Downstream of the reactor, the products obtained were cooled in a heat exchanger and the condensed liquid was collected in glass vials by means of a series of timer-controlled valves. The uncondensed gases, on the other hand, were passed through a volumetric wet gas meter in order to measure the volume of gases produced. A small proportion of the gases was sampled in an on-line gas chromatograph (GC) for analysis. On-line analysis of the gases was performed by an Agilent HP7890 gas chromatograph (GC) with an HP-Al/S column (length 50 m; diameter 0.53 mm; film thickness 15 micron), the carrier gas used was helium flowing at 30 cm/s, the detector was a flame detector. Gas analysis was performed using an external standard with calibration curves for the individual known components.

The collected liquids were characterised by means of gas chromatographic analysis using an Agilent HP6890 gas chromatograph (GC) equipped with a "split/splitless" injector on a Quadrex 007 FFAP column (height 25 m; diameter 0.32 mm; film thickness 1 micron), the carrier gas used was helium with a velocity of 50 cm/s, the detector was a flame detector. Determination was performed using an internal standard with calibration curves for the individual known components.

The catalytic performance values shown in the following tables are expressed by calculating the conversion of 1,3-butanediol [1,3-BDO] ($C_{1,3\text{-}BDO}$) and the selectivities for the various products ($S_i$) according to the formulae shown below.

$$C_{1,3\text{-}BDO} = \frac{(\text{mol}_{1,3\text{-}BDO})_{in} - (\text{mol}_{1,3\text{-}BDO})_{out}}{(\text{mol}_{1,3\text{-}BDO})_{in}} \times 100$$

$$S_i = \frac{\text{mol}_i}{(\text{mol}_{1,3\text{-}BDO})_{in} - (\text{mol}_{1,3\text{-}BDO})_{out}} \times 100$$

The catalyst obtained as described in Example 1 (Ex. 1 cat.) in a first test, the catalyst obtained as described in Example 2 (Ex. 2 cat.) in a second test, and the catalyst obtained as described in Example 3 (Ex. 3 cat.) in a third test, ground and sieved to obtain the 0.5 mm to 1 mm fraction, was charged into the reactor and subsequently pre-treated in situ, at 300° C., under a stream of nitrogen ($N_2$).

30 g/h of 1,3-butanediol (Fluka, purity ≥99%) together with nitrogen ($N_2$) in a 1,3-butanediol:nitrogen ($N_2$) ratio equal to 1 were then fed into the above-stated reactor. The test was carried out at a space velocity relative to 1,3-butanediol ("Weight Hourly Space Velocity") equal to 10 $h^{-1}$, at atmospheric pressure (1 bara), and at gradually rising temperatures: each sample was taken after six hours at the stated temperature.

Table 1 shows the catalytic results obtained in terms of conversion (C %) and selectivity (S %), calculated as described above, at the various temperatures.

TABLE 1

| | 1,3-Butanediol conversion (C %) | Selectivity | | | |
|---|---|---|---|---|---|
| | | 3-buten-2-ol (S %) | 2-buten-1-ol (S %) | 3-buten-1-ol (S %) | 1,3-butadiene (S %) |
| Ex. 1 cat. temperature (° C.) | | | | | |
| 300 | 16 | 37 | 25 | 0.0 | 0.1 |
| 325 | 33 | 56 | 39 | 0.0 | 0.0 |
| 350 | 70 | 54 | 39 | 0.2 | 0.0 |
| 375 | 93 | 56 | 37 | 0.6 | 0.0 |
| 400 | 98 | 55 | 29 | 1.2 | 0.0 |
| Ex. 2 cat. temperature (° C.) | | | | | |
| 300 | 13 | 45 | 32 | 0.0 | 0.0 |
| 325 | 39 | 54 | 39 | 0.0 | 0.0 |
| 350 | 77 | 54 | 39 | 0.2 | 0.0 |
| 375 | 98 | 53 | 38 | 0.4 | 0.0 |
| 400 | >99 | 53 | 31 | 1.1 | 0.0 |
| Ex. 3 cat. temperature (° C.) | | | | | |
| 300 | 43 | 58 | 42 | 0.0 | 0.1 |
| 325 | 77 | 55 | 40 | 0.2 | 0.1 |
| 350 | 97 | 54 | 38 | 0.4 | 0.4 |

TABLE 1-continued

| | 1,3-Butanediol conversion (C %) | Selectivity | | | |
|---|---|---|---|---|---|
| | | 3-buten-2-ol (S %) | 2-buten-1-ol (S %) | 3-buten-1-ol (S %) | 1,3-butadiene (S %) |
| 375 | >99 | 53 | 32 | 0.9 | 1.2 |
| 400 | >99 | 53 | 20 | 1.6 | 3.7 |

It is evident from the data shown in Table 1 that the process provided by the present invention in which the catalysts obtained as described in Example 1 (Ex. 1 cat.), Example 2 (Ex. 2 cat.) and Example 3 (Ex. 3 cat.) were used is capable of providing elevated conversions and selectivities over a wide temperature range. It is furthermore evident that an increase in the surface area of said catalysts has no negative impact on selectivity over a broad range of temperatures and of conversions.

EXAMPLE 5

Preparation of a Catalyst Based on Cerium Oxide in the Presence of a Base

A solution of 87 g of cerium nitrate hexahydrate (99% Aldrich; product code 238538; CAS Number 10294-41-4) in 420 g of water was prepared by vigorous stirring, at room temperature (25° C.), in a 1 liter beaker equipped with a magnetic stirrer bar. With vigorous stirring being maintained, 75 g of a 15% aqueous ammonium hydroxide ($NH_4OH$) solution, previously prepared by diluting the 28%-30% commercial aqueous solution (Aldrich 28%-30% $NH_3$ Basis ACS reagent; product code 221228, CAS Number 1336-21-6), were added to the resultant solution over a period of 25 minutes by means of a peristaltic pump, with pH being monitored by way of a Hamilton LIQ-GAS combined glass laboratory pH electrode connected to a EUTECH Instruments pH1500 pH meter. On completion of the addition of said solution, a suspension having a pH equal to 9.0 was obtained. Vigorous stirring of the mixture was continued for 64 hours. Subsequently, with vigorous stirring being maintained, a further 25 g of a 15% aqueous ammonium hydroxide ($NH_4OH$) solution, previously prepared as described above, were added to the resultant suspension, having a pH equal to 4, over a period of 10 minutes by means of a peristaltic pump, a suspension having a pH equal to 9.0 being obtained. The suspension was vigorously stirred for a further 24 hours, at the end of which period the pH was remeasured and found to be equal to 8.8, and a precipitate was obtained. The resultant precipitate was filtered, washed with 500 ml of water, and subsequently dried in an oven at 120° C. for 2 hours. After drying, the resultant solid was calcined for 6 hours at 600° C. The XRD spectrum of the solid obtained after calcination revealed the formation of a catalyst based on crystalline cerium oxide (identified by comparison with reference card 04-008-6551 present in the PDF-4 database which has already been mentioned above). The resultant catalyst based on cerium oxide had a BET specific surface area, determined as mentioned above, equal to 18 $m^2/g$.

EXAMPLE 6

Preparation of Alkenols from 1,3-Butanediol

The catalyst (3 g) obtained as described in Example 5 (Ex. 5 cat.), ground and sieved to obtain the 0.5 mm to 1 mm fraction, was charged into the reactor, proceeding as described in Example 4, and subsequently pre-treated in situ, at 350° C., under a stream of nitrogen ($N_2$).

24.5 g/h of 1,3-butanediol (Fluka, purity 99%) together with nitrogen ($N_2$) in a 1,3-butanediol:nitrogen ($N_2$) ratio equal to 1 were then fed into the above-stated reactor. The test was carried out at atmospheric pressure (1 bara) and at a temperature of 350° C. Table 2 shows the catalytic results obtained in terms of conversion (C %) and selectivity (S %), calculated as described above, at the various reaction times: each sample was taken during the 6 hours preceding the time stated in Table 2.

TABLE 2

| Ex. 5 cat. reaction time (hours) | 1,3-Butanediol conversion (C %) | Selectivity | | | |
|---|---|---|---|---|---|
| | | 3-buten-2-ol (S %) | 2-buten-1-ol (S %) | 3-buten-1-ol (S %) | 1,3-butadiene (S %) |
| 23 | 97 | 53 | 38 | 0.3 | 0.3 |
| 60 | 97 | 54 | 38 | 0.3 | 0.4 |
| 160 | 94 | 54 | 38 | 0.3 | 0.5 |
| 302 | 97 | 55 | 40 | 0.3 | 0.7 |
| 486 | 97 | 55 | 39 | 0.4 | 0.6 |

It is evident from the data shown in Table 2 that the process provided by the present invention in which the catalyst obtained as described in Example 5 (Ex. 5 cat.) was used is capable of providing elevated conversions and selectivities and that said catalyst is stable even at elevated temperatures, for extended periods, despite the low diluent content [i.e. nitrogen ($N_2$)]. It is furthermore evident that said catalyst has elevated productivity (said productivity being taken to mean the total quantity of butenols produced per unit of catalyst during the test) well above, for example, one kg of alkenols/g of catalyst, without obvious signs of deactivation.

EXAMPLE 7

Preparation of Alkenols from 1,3-Butanediol

The catalyst (3 g) obtained as described in Example 5 (Ex. 5 cat.), ground and sieved to obtain the 0.5 mm to 1 mm fraction, was charged into a reactor, operating as described in Example 4, and subsequently pre-treated in situ, at 350° C., under a stream of nitrogen ($N_2$).

The catalyst was then subjected to life testing using a method entirely similar to that described in Example 6 with the sole difference that water was fed as diluent instead of nitrogen ($N_2$).

30.7 g/h of 1,3-butanediol (Fluke, purity 99%) in water in an amount of 82.5%, equivalent to a 1,3-butanediol:water ratio equal to 1, were then fed into the above-stated reactor.

The test was carried out at atmospheric pressure (1 bara) and at a temperature of 350° C. Table 3 shows the catalytic results obtained in terms of conversion (C %) and selectivity (S %), calculated as described above, at the various reaction times: each sample was taken during the 6 hours preceding the time stated in Table 3.

TABLE 3

| Ex. 5 cat. reaction time (hours) | 1,3-Butanediol conversion (%) | Selectivity | | | |
|---|---|---|---|---|---|
| | | 3-buten-2-ol (S %) | 2-buten-1-ol (S %) | 3-buten-1-ol (S %) | 1,3-butadiene (S %) |
| 22 | 88 | 56 | 39 | 0.3 | 0.1 |
| 192 | 90 | 57 | 39 | 0.3 | 0.1 |
| 252 | 92 | 57 | 39 | 0.4 | 0.2 |
| 312 | 93 | 57 | 39 | 0.4 | 0.1 |
| 572 | 96 | 57 | 39 | 0.4 | 0.2 |

It is evident from the data shown in Table 3 that the process provided by the present invention in which the catalyst obtained as described in Example 5 was used is capable of providing elevated conversions and selectivities and that said catalyst is stable even at elevated temperatures, for extended periods, despite the low diluent content [i.e. $H_2O$]. It is furthermore evident that said catalyst has elevated productivity (said productivity being taken to mean the total quantity of butenols produced per unit of catalyst during the test) well above, for example, one kg of alkenols/g of catalyst, without obvious signs of deactivation.

EXAMPLE 8

Preparation of Alkenols from 1,3-Butanediol

The catalyst obtained as described in Example 2 (Ex. 2 cat.), ground and sieved to obtain the 0.5 mm to 1 mm fraction, was charged into a reactor, operating as described in Example 4, and subsequently pre-treated in situ, at 400° C., under a stream of nitrogen ($N_2$).

29.5 g/h of 1,3-butanediol (Fluka, purity ≥99%) together with nitrogen ($N_2$) in a 1,3-butanediol:nitrogen ($N_2$) ratio equal to 1 were then fed into the above-stated reactor. The test was carried out at a space velocity relative to 1,3-butanediol ("Weight Hourly Space Velocity") equal to 10 $h^{-1}$, at atmospheric pressure (1 bara), and at a temperature of 400° C.

Table 4 shows the catalytic results obtained in terms of conversion (C %) and selectivity (S %) at the various reaction times: each sample was taken during the 6 hours preceding the time stated in Table 4.

TABLE 4

| Ex. 2 cat. reaction time (hours) | 1,3-Butanediol conversion (%) | Selectivity | | | |
|---|---|---|---|---|---|
| | | 3-buten-2-ol (S %) | 2-buten-1-ol (S %) | 3-buten-1-ol (S %) | 1,3-butadiene (S %) |
| 146 | >99 | 52 | 34 | 0.8 | 1.9 |
| 162 | >99 | 53 | 36 | 0.6 | 1.8 |
| 246 | >99 | 52 | 36 | 0.7 | 1.7 |
| 301 | 98 | 52 | 37 | 0.6 | 1.4 |

It is evident from the data shown in Table 4 that the process provided by the present invention in which the catalyst obtained as described in Example 2 (Ex. 2 cat.) was used is capable of providing elevated conversions and selectivities and that said catalyst is stable for extended periods even at elevated temperatures, despite the low diluent content [i.e. nitrogen ($N_2$)].

EXAMPLE 9

Preparation of a Catalyst Based on Extruded Cerium Oxide

A solution of 870 g of cerium nitrate hexahydrate (99% Aldrich; product code 238538; CAS Number 10294-41-4) in 4200 g of water was prepared by vigorous stirring, at room temperature (25° C.), in a glass beaker equipped with a magnetic stirrer bar. The resultant solution was transferred into a glass reactor equipped with an anchor stirrer and stirring was maintained for 15 minutes. With stirring being maintained, 790 g of an aqueous 15% ammonium hydroxide ($NH_4OH$) solution, previously prepared by diluting the 28%-30% commercial aqueous solution (Aldrich 28%-30% $NH_3$ Basis ACS reagent; product code 221228, CAS Number 1336-21-6), were added to the resultant solution over a period of 3 hours by means of a peristaltic pump, with pH being monitored by way of a Metrohm glass pH electrode, 6.0248.030, connected to a Metrohm 691 pH meter. On completion of the addition of said solution, the pH of the suspension was equal to 9.0: stirring of the mixture was continued for 64 hours, at the end of which period the pH was equal to 4.3. Subsequently, with stirring being maintained, a further 90 g of a 15% aqueous ammonium hydroxide ($NH_4OH$) solution, previously prepared as described above, were added to the resultant suspension over a period of 25 minutes by means of a peristaltic pump, a suspension with a pH equal to 9.0 being obtained. The suspension was vigorously stirred for a further 24 hours, at the end of which period the pH was remeasured and found to be equal to 8.8, and a precipitate was obtained. The resultant precipitate was filtered, washed with about 10 liters of water, and subsequently dried in an oven at 120° C. for 2 hours.

After having repeated the above-stated preparation for an appropriate number of batches to obtain sufficient quantities of material, the resultant solids were combined and ground in a mortar: 1905 g of powder obtained in this manner were then place in Erweka planetary mixer with an AMD model motor.

The powder was dry mixed for 1 hour and the following were subsequently added dropwise in succession, 250 g of a 25% aqueous ammonium hydroxide ($NH_4OH$) solution, previously prepared by diluting the commercial aqueous 28%-30% solution (28%-30% $NH_3$ Basis ACS reagent Aldrich; product code 221228; CAS Number 1336-21-6), over a period of 50 minutes and 250 ml of demineralised water, likewise over a period of 50 minutes, a paste being obtained which was extruded with a Hutt extruder fitted with rollers having 2 mm holes. The resultant pellets obtained by extrusion were allowed to dry in air for two days.

Subsequently, a sample of the pellets weighing 134 g was oven-dried at 120° C. for 2 hours and subsequently calcined for 6 hours at 600° C., a catalyst based on cerium oxide being obtained.

The resultant catalyst based on cerium oxide had a BET specific surface area, determined as mentioned above, equal to 18 m²/g.

EXAMPLE 10

Preparation of Alkenols from 1,3-Butanediol with Catalyst Based on Extruded Cerium Oxide The catalyst obtained as described in Example 9 (Ex. 9 cat.), ground and sieved to obtain the 0.5 mm to 1 mm fraction, was charged into a reactor, operating as described in Example 4, and subsequently pre-treated in situ, at 400° C., under a stream of nitrogen ($N_2$).

28.8 g/h of 1,3-butanediol (Fluka, purity ≥99%) together with nitrogen ($N_2$) in a 1,3-butanediol:nitrogen ($N_2$) ratio equal to 1 were then fed into the above-stated reactor. The test was carried out at a space velocity relative to 1,3-butanediol ("Weight Hourly Space Velocity") equal to 10 $h^{-1}$, at atmospheric pressure (1 bara), and at a temperature of 400° C.

Table 5 shows the catalytic results obtained in terms of conversion (C %) and selectivity (S %) at the various reaction times: each sample was taken during the 6 hours preceding the time stated in Table 5.

TABLE 5

| Ex. 9 cat. | | Selectivity | | | |
|---|---|---|---|---|---|
| reaction time (hours) | 1,3-Butanediol conversion (%) | 3-buten-2-ol (S %) | 2-buten-1-ol (S %) | 3-buten-1-ol (S %) | 1,3-butadiene (S %) |
| 90 | >99 | 51 | 30 | 0.9 | 2.8 |
| 187 | >99 | 53 | 34 | 1.0 | 2.8 |
| 283 | 99 | 52 | 38 | 0.6 | 1.8 |
| 348 | 98 | 52 | 39 | 0.6 | 1.3 |

It is evident from the data shown in Table 5 that the process provided by the present invention in which the catalyst obtained as described in Example 9 (Ex. 9 cat.) was used is capable of providing elevated conversions and selectivities and that said catalyst is stable even at elevated temperatures and also at low diluent contents [i.e. nitrogen ($N_2$)]. It should furthermore be noted that said catalyst performs substantially similarly to those catalysts which have not been subjected to forming operations.

EXAMPLE 11

Preparation of a Catalyst Based on Silica-Alumina 7.6 g of aluminium tri-sec-butoxide (97% Aldrich; product code 201073; CAS Number 2269-22-9) were introduced into a 500 ml, 2-necked flask. A solution of 50 g of silicic acid (99.9% Aldrich; product code 288772; CAS Number 1343-98-2) with 250 g of deionised water was then prepared by vigorous stirring in a 500 ml conical flask. Using a suitable dropping funnel, the solution was then transferred in 10 minutes into the above-mentioned flask containing the alumina precursor, while the mixture was vigorously stirred. Once addition was complete, the solution was vigorously stirred for 1 hour. After 1 hour, the temperature was adjusted to 90° C. and the solution was kept at said temperature for 1 hour. The resultant suspension was filtered and washed with 5 liters of deionised water, a precipitate being obtained which was oven-dried at 120° C. for 12 hours. After drying, the resultant solid was calcined at 550° C. in a muffle furnace for 5 hours.

Elemental analysis of the solid after calcination performed by WD-XRF (Wavelength dispersion X-Ray fluorescence) using a PANalytical Axios Advanced spectrometer equipped with a 4 kW X-ray tube with Rh anode, revealed the formation of a solid having an $Al_2O_3$ content equal to 3.8%.

Subsequently, a part of the solid obtained as described above, designated active phase, was bound with alumina (Versal V250-UOP).

To this end, 40.4 g of active phase were placed in an 800 ml beaker with 24.4 g of alumina (Versal V250-UOP). The powders were mixed mechanically, then 302 g of a 4% acetic acid solution, previously produced by diluting the >99.7% commercial aqueous solution (Aldrich >99.7% acetic acid ACS reagent; product code 320099; CAS Number 64-19-7), were added. The resultant suspension was heated to 60° C. and kept at said temperature with vigorous stirring for 2 hours. The suspension, with vigorous stirring still being continued, was then heated to 150° C., and allowed to dry at said temperature for 12 hours, a dry product being obtained which was transferred into a porcelain evaporating dish and placed in a muffle furnace to calcine at 550° C. for 5 hours.

EXAMPLE 12

Preparation of 1,3-Butadiene from Butenols

The catalyst obtained as described in Example 11 was used in a dehydration test of a mixture of butenols and water.

To this end, the mixtures of butenols obtained as described in Example 4 and Example 5 were combined to obtain a mixture which was distilled to obtain an aqueous solution of isomeric butenols having the composition shown in Table 6.

TABLE 6

|  | Composition (%) |
| --- | --- |
| 2-Buten-1-ol | 14 |
| 3-Buten-2-ol | 50 |
| 3-Buten-1-ol | 0.4 |
| Water | 35 |

The catalyst obtained as described in Example 11 (Ex. 11 cat.), ground and sieved to obtain the 0.5 mm to 1 mm fraction, was charged into a reactor, operating as described in Example 4, and subsequently pre-treated in situ, at 300° C., under a stream of nitrogen ($N_2$).

27.8 g/h of the aqueous solution of isomeric butenols shown in Table 6 and 7.4 Nl/h of nitrogen ($N_2$) were then fed into the above-stated reactor.

The catalytic results obtained were expressed in terms of conversion and selectivity. The calculations were performed using formulae similar to those stated above for the diol dehydration stage, taking as the starting reactant the sum of butenols present in the mixture and calculating the selectivity by taking account of the number of mol of 1,3-butadiene obtained.

After 2 hours of reaction at 300° C., the reactivity values were as follows:

butenol conversion (C %): 99%;
selectivity for 1,3-butadiene (S %): 91%.

It is evident from the data shown above that the process provided by the present invention is capable of producing mixtures of butenols which may subsequently be used in the production of 1,3-butadiene with excellent conversion (C %) and selectivity (S %) values.

EXAMPLE 13

Preparation of 1,3-Butadiene from Butenols

The catalyst obtained as described in Example 11 (Ex. 11 cat.) was used in a dehydration test of a mixture of butenols and water.

For this purpose, the catalyst (3 g) obtained as described in Example 11 (Ex. 11 cat.), ground and sieved to obtain the 0.5 mm to 1 mm fraction, was charged into a reactor, operating as described in Example 4, and subsequently pre-treated in situ, at 300° C., under a stream of nitrogen ($N_2$).

27.8 g/h of the aqueous solution of butenols shown in Table 6 and 7.4 Nl/h of nitrogen ($N_2$) were then fed into the above-stated reactor.

The catalytic results obtained at 400° C., stated in terms of conversion and selectivity, after 2 hours, 4 hours and 6 hours of reaction, are shown in Table 7.

TABLE 7

| Ex. 11 cat. reaction time (hours) | Butenol conversion (C %) | Selectivity for 1,3-butadiene (S %) |
| --- | --- | --- |
| 2 | 100 | 82 |
| 4 | 100 | 91 |
| 6 | 100 | 92 |

It is evident from the data shown above that the process provided by the present invention is capable of producing mixtures of butenols which may subsequently be used in the production of 1,3-butadiene with excellent conversion (C %) and selectivity (S %) values.

The invention claimed is:

1. Process for the production of alkenols comprising:
dehydrating 1,3-butanediol in the presence of at least one catalyst based on cerium oxide in at least one diluent at a process temperature ranging from 300° C. to 430° C. to produce alkenols;
wherein said catalyst based on cerium oxide is obtained by precipitation, in the presence of at least one base, of at least one compound containing cerium;
wherein said catalyst based on cerium oxide is pre-treated at a temperature the same as said process temperature before said dehydrating;
said dehydrating being carried out in said at least one diluent selected from: inert gas; or from a compound having a boiling point greater than or equal to 50° C. and a melting temperature of less than or equal to 40° C. as follows:
in the case in which the diluent is selected from said inert gas, at a molar ratio between diol and diluent of at least 0.5;
in the case in which the diluent is selected from said compound having a boiling point greater than or equal to 50° C. and a melting temperature of less than or equal to 40° C., at a molar ratio between diol and diluent ranging from 0.4 to 100.

2. Process for the production of alkenols according to claim 1, wherein said catalyst based on cerium oxide is obtained by a process comprising:
preparing a solution including at least one compound containing cerium;
adding to said solution at least one base in a time ranging from 1 minute to 16 hours to obtain a reaction mixture;
allowing said reaction mixture to react at a temperature ranging from 15° C. to 100° C., for a time ranging from 1 minute to 120 hours, to obtain a precipitate;
recovering the precipitate and subjecting it to drying and, optionally, to calcination.

3. Process for the production of alkenols according to claim 1, wherein said catalyst based on cerium oxide is obtained by a process comprising:

preparing a solution including at least one base;
adding to said solution at least one compound containing cerium in a time ranging from 1 minute to 16 hours, to obtain a reaction mixture;
allowing said reaction mixture to react at a temperature ranging from 15° C. to 100° C., for a time ranging from 1 minute to 120 hours, to obtain a precipitate;
recovering the precipitate and subjecting it to drying and, optionally, to calcination.

4. Process for the production of alkenols according to claim 2, wherein said solution including at least one compound containing cerium or said solution including at least one base, is an aqueous solution comprising from 5% by weight to 70% by weight, relative to the total weight of said aqueous solution, of at least one compound containing cerium or of at least one base.

5. Process for the production of alkenols according to claim 2, wherein said solution including at least one compound containing cerium or said solution including at least one base is a water-alcohol solution comprising from 5% by weight to 95% by weight, relative to the total weight of said water-alcohol solution, of at least one alcohol selected from ethanol, 2-methoxyethanol, n-propanol, iso-propanol, n-butanol, iso-butanol, tert-butanol, or mixtures thereof.

6. Process for the production of alkenols according to claim 1, wherein said cerium containing compound is selected from: soluble cerium salts; or cerium alkoxides.

7. Process for the production of alkenols according to claim 2, wherein, in the case in which said solution containing at least one compound containing cerium mainly comprises cerium(III), at least one oxidising agent is added to said solution.

8. Process for the production of alkenols according to claim 2, wherein, in the case in which said solution containing at least one compound containing cerium mainly comprises cerium(III), the recovered precipitate, before being subjected to drying and, optionally, calcination, is treated with at least one oxidising agent.

9. Process for the production of alkenols according to claim 1, wherein said base is selected from: hydroxides of alkali metals or alkaline earth metals; secondary or tertiary amines; quaternary ammonium salts; ammonium hydroxide (NH$_4$OH), urea.

10. Process for the production of alkenols according to claim 9, wherein said base is selected from aqueous solutions of: ammonium hydroxide (NH$_4$OH), triethylamine, tetrapropylammonium hydroxide.

11. Process for the production of alkenols according to claim 1, wherein said catalyst based on cerium oxide has a specific surface area ranging from 0.5 m$^2$/g to 250 m$^2$/g.

12. Process for the production of alkenols according to claim 1, wherein said catalyst based on cerium oxide is used in the form of an extrudate, optionally containing conventional binders.

13. Process for the production of alkenols according to claim 1, wherein said diol is bio-1,3-butanediol derived from the fermentation of sugars.

14. Process for the production of alkenols according to claim 1, wherein said diol is bio-1,3-butanediol derived from the fermentation of sugars derived from guayule or thistle, including discards, residues or waste arising from said guayule and/or thistle or the processing thereof.

15. Process for the production of alkenols according to claim 1, wherein said process for the production of alkenols is carried out at a pressure ranging from 0.05 bara to 50 bara.

16. Process for the production of alkenols according to claim 1, wherein said process for the production of alkenols is carried out using a "Weight Hourly Space Velocity" (WHSV), which is a ratio between the weight of the diol fed in one hour and the weight of catalyst based on cerium oxide, said ratio being measured in h$^{-1}$, ranging from 0.5 h$^{-1}$ to 20 h$^{-1}$.

17. Process for the production of 1,3-butadiene comprising bringing at least one of the alkenols obtained with the process of claim 1, into contact with at least one catalyst, under suitable conditions for the dehydration of said at least one alkenol.

18. Process for the production of 1,3-butadiene according to claim 17, wherein said catalyst is selected from solid acid catalysts.

19. Process for the production of alkenols comprising:
providing a catalyst based on cerium oxide by a process including:
  providing at least one cerium containing compound;
  providing a first addition of at least one base;
  wherein said at least one cerium containing compound and said at least one base are mixed to form a reaction mixture at a pH of at least 9.0;
  allowing said reaction mixture to react until decreasing to a pH of about 4.0;
  providing a second addition of said base such that said reaction mixture reaches a pH of 9.0;
  allowing said reaction mixture to react until a precipitate is formed and recovered to form said catalyst based on cerium oxide; and
dehydrating 1,3-butanediol in a presence of said catalyst based on cerium oxide and a diluent at a process temperature ranging from 300° C. to 430° C. to produce alkenols, said diluent being selected from: inert gas, or from a compound having a boiling point greater than or equal to 50° C. and a melting temperature of less than or equal to 40° C.;
said dehydrating being carried out as follows:
  in the case in which the diluent is selected from said inert gas, at a molar ratio between diol and diluent of at least 0.5;
  in the case in which the diluent is selected from said compound having a boiling point greater than or equal to 50° C. and a melting temperature of less than or equal to 40° C., at a molar ratio between diol and diluent ranging from 0.4 to 100.

20. Process for the production of alkenols according to claim 19, wherein said diol is bio-1,3-butanediol derived from the fermentation of sugars.

21. Process for the production of alkenols according to claim 19, wherein said diol is bio-1,3-butanediol derived from the fermentation of sugars derived from guayule or thistle, including discards, residues or waste arising from said guayule and/or thistle or the processing thereof.

22. Process for the production of alkenols according to claim 19 wherein said base is selected from: hydroxides of alkali metals or alkaline earth metals; secondary or tertiary amines; quaternary ammonium salts; ammonium hydroxide (NH$_4$OH), urea.

23. Process for the production of alkenols according to claim 22 wherein said cerium containing compound is cerium nitrate.

* * * * *